(12) United States Patent
Modi

(10) Patent No.: US 11,298,336 B2
(45) Date of Patent: Apr. 12, 2022

(54) WATER SOLUBLE FORMULATION

(71) Applicant: Pankaj Modi, Ancaster (CA)

(72) Inventor: Pankaj Modi, Ancaster (CA)

(73) Assignee: Soluble Technologies, Inc., White Plains, NY (US)

( * ) Notice: Subject to any disclaimer, the term of this patent is extended or adjusted under 35 U.S.C. 154(b) by 187 days.

(21) Appl. No.: 16/426,649

(22) Filed: May 30, 2019

(65) Prior Publication Data

US 2020/0375938 A1 Dec. 3, 2020

(51) Int. Cl.
| | |
|---|---|
| *A61K 31/352* | (2006.01) |
| *A61K 38/46* | (2006.01) |
| *A61K 9/00* | (2006.01) |
| *A61K 47/20* | (2006.01) |
| *A61K 47/26* | (2006.01) |
| *A61K 47/34* | (2017.01) |
| *A61K 47/36* | (2006.01) |
| *A61K 47/12* | (2006.01) |
| *A61K 47/22* | (2006.01) |
| *A23L 2/52* | (2006.01) |
| *A61K 47/14* | (2017.01) |

(52) U.S. Cl.
CPC .............. *A61K 31/352* (2013.01); *A23L 2/52* (2013.01); *A61K 9/0019* (2013.01); *A61K 9/0095* (2013.01); *A61K 38/465* (2013.01); *A61K 47/12* (2013.01); *A61K 47/14* (2013.01); *A61K 47/20* (2013.01); *A61K 47/22* (2013.01); *A61K 47/26* (2013.01); *A61K 47/34* (2013.01); *A61K 47/36* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,439,686 | A | 8/1995 | Desai et al. |
| 5,989,583 | A | 11/1999 | Amselem |
| 6,350,458 | B1 | 2/2002 | Modi |
| 6,849,263 | B2 | 2/2005 | Modi |
| 8,623,401 | B2 | 1/2014 | Modi |
| 10,555,901 | B2 | 2/2020 | Zhao et al. |
| 2009/0117180 | A1 | 5/2009 | Orenz et al. |
| 2012/0231083 | A1 | 9/2012 | Carley |

FOREIGN PATENT DOCUMENTS

| | | |
|---|---|---|
| CA | 2194890 | 1/1996 |
| CA | 2222120 | 12/1996 |
| CA | 2268187 | 4/1998 |
| CA | 2229286 | 8/1999 |
| CA | 2354148 | 6/2000 |
| CA | 2382535 | 3/2001 |
| CA | 2391923 | 5/2001 |
| CA | 2428535 | 6/2002 |
| CA | 2493786 | 2/2004 |
| CA | 2518918 | 11/2004 |
| CA | 2589993 | 6/2006 |
| CA | 2624110 | 11/2010 |
| CA | 2922959 | 6/2016 |
| CA | 3020798 | 10/2017 |
| CA | 3053158 | 8/2018 |
| CA | 3059056 | 12/2018 |
| CA | 3061086 | 5/2020 |
| EP | 1897543 | 3/2008 |
| WO | 2001072278 | 4/2001 |
| WO | 200172278 | 10/2001 |
| WO | 2004043445 | 5/2004 |
| WO | 2007062494 | 6/2007 |
| WO | 2009015456 | 2/2009 |
| WO | 2010002418 | 1/2010 |
| WO | 2013009928 | 1/2013 |
| WO | 2015068052 | 5/2015 |

OTHER PUBLICATIONS

European Search Report—EP 17759030.4.
Pathare et al.—"Polymers used for Fast Disintegrating Oral Films: A Review", Int. J. Pharm. Sci. Rev. Res., 21(1), Jul.-Aug. 2013; No. 29, 169-178.
Shrestha et al.—"Nanoparticle processing: Understanding and controlling aggregation", Advances in Coolid and Interface Science, 279 (2020) 102162.
Smith et al.—"Dispursing nanoparticles in a polymer matrix: are long, dense polymer tethers really necessary?", Langmuir, Oct. 6, 2009:25 (19); 11239-43.
Liu et al.—"Nanoparticle Dispersion and Aggregation in Polymer Nanocomposites: Insights from Molecular Dynamics Simulation", Langmuir, 2011, 27, 7926-7933.
Lv et al.—"Mucoadhesive bucal films containing phospholipid-bile salts-mixed micelles as an effecitve carrier for Cucurbitacin B delivery", Drug Deliv, 2015; 22(3):351-358.
International Search Report PCT/CA2020/050737—dated Aug. 18, 2020.
Written Opinion PCT/CA2020/050737—dated Aug. 18, 2020.
Kelapu, S. et al.—Insoluble Drug Delivery Strategies: Review of Recent Advances and Business Prospects, Acta Pharm Sin B. Sep. 2015, vol. 5, No. 5, pp. 442-453 ISSN 2211-3835.
Singh et al.—Oral Formulation Strategies to Improve Solubility of Poorly Water Soluble Drugs, Expert Opin Drug Deliv, Oct. 2011, vol. 8, No. 10, pp. 1361-1378 ISSN 1744-5247.

*Primary Examiner* — Michael Barker
(74) *Attorney, Agent, or Firm* — Gowling WLG (Canada) LLP

(57) ABSTRACT

A formulation for solubilizing a water insoluble pharmaceutical agent is provided. The formulation comprises: a water-insoluble pharmaceutical agent, a detergent, an enzyme that breaks down lipids, proteins, and/or starches, a plasticizing agent, an emulsifying agent and an aqueous solvent. A method of making the formulation is also provided.

20 Claims, 1 Drawing Sheet

1) Aminoalkylindoles
a) Naphthoylindoles
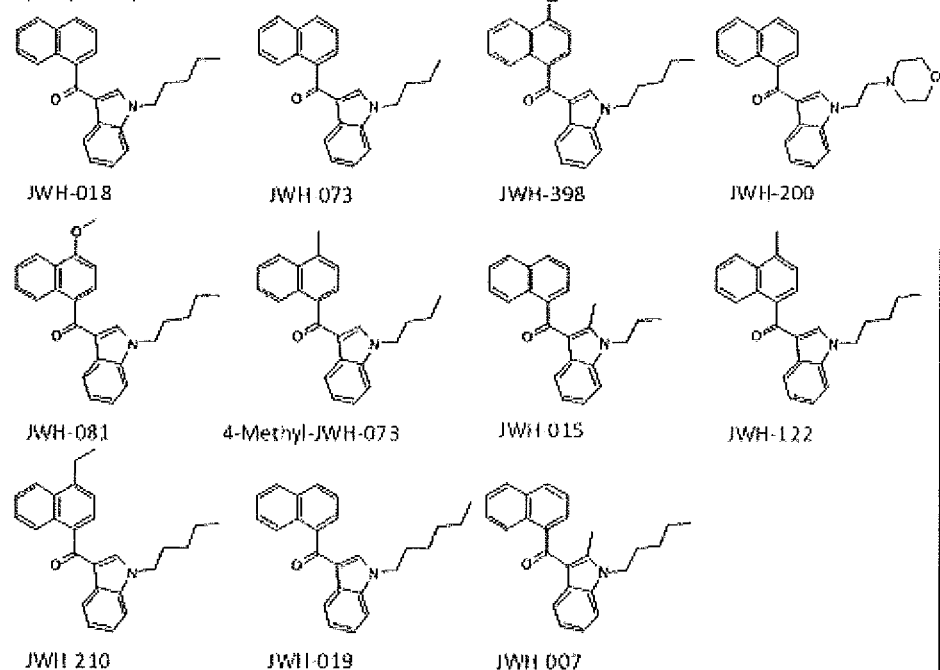
JWH-018  JWH-073  JWH-398  JWH-200
JWH-081  4-Methyl-JWH-073  JWH-015  JWH-122
JWH-210  JWH-019  JWH-007
b) Phenylacetylindoles
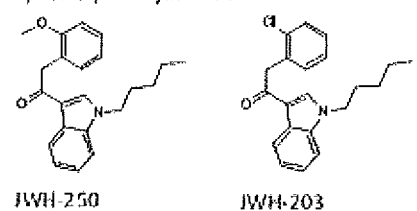
JWH-250  JWH-203
c) Benzoylindoles
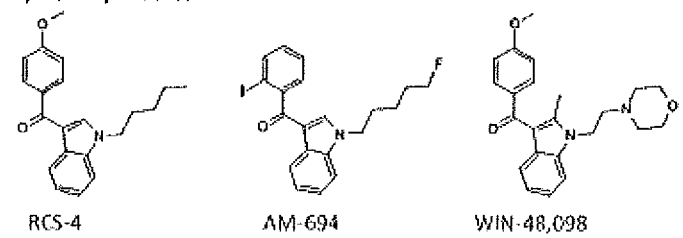
RCS-4  AM-694  WIN-48,098
2) Cyclohexylphenoles
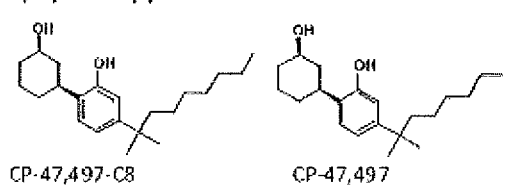
CP-47,497-C8  CP-47,497
3) Classical cannabinoids
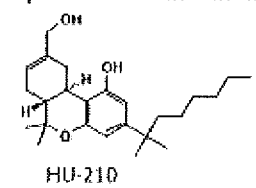
HU-210

WATER SOLUBLE FORMULATION

FIELD OF THE INVENTION

The present invention generally relates to water soluble formulations, and more particularly relates to water soluble formulations comprising a pharmaceutical agent that is water insoluble or poorly soluble, such as a cannabinoid, and methods of preparing such formulations.

BACKGROUND OF THE INVENTION

Cannabis compounds have a long history of use in humans as an anticonvulsant, sedative, hypnotic, anti-depressant, analgesic, anti-inflammatory, anti-emetic, anti-spasmodic, and appetite-stimulator. Cannabis contains a broad spectrum of chemical compounds including: phytocannabinoids, terpenoids (essential oils), flavonoids, enzymes, and steroids. While delta-9-tetrahydrocannabinol (delta-9-THC) is believed to be the principle psychoactive component of hemp, other phytocannabinoids (such as cannabidiol, cannabinol, and cannabichromene) are thought to possess numerous medicinal properties without the psychoactive effects of delta-9-THC.

However, the oral bioavailability of such phytocannabinoids is limited. For example, the oral bioavailability of cannabinoids was found to be about 6% or less. The limited bioavailability of phytocannabinoids is believed to be due to the fact that cannabinoids are naturally hydrophobic, fat-soluble compounds which limits their absorption, thereby substantially decreasing their bioavailability.

Due to the many desirable properties of phytocannabinoids, it would be advantageous to provide phytocannabinoid formulations with enhanced bioavailability for human consumption in various convenient dosage forms.

U.S. Pat. No. 6,045,826 discloses water-soluble compositions containing a lipophilic compound (including CoQ10) and a single solubilizing agent having both hydrophobic and hydrophilic moieties. Other formulations useful for the delivery of coenzyme Q (CoQ10) are described in U.S. Pat. No. 7,438,903 which teaches that soft gels are the most popular method of CoQ10 delivery, and CoQ10 is available commercially in the form of tablets, hard capsules and softgel capsules, either alone or in combination with vitamins and/or supplements. U.S. Pat. No. 4,483,873 discloses aqueous solutions of CoQ10 that contain hydrogenated lecithin to increase CoQ10 bioavailability. U.S. Pat. Nos. 6,056,971, 6,441,050 and 7,094,804 disclose methods for solubilizing water-insoluble dietary supplements in liquid form, such as CoQ10 in a softgel, by mixing CoQ10 with, among other things, an edible polyhydric alcohol solvent. U.S. Pat. No. 6,300,377 teaches the formulation of a CoQ10 composition that omits polyhydric alcohol, but includes other agents to help improve solubility, including a glyceryl ester molecule having one to three $C_2$-$C_7$ acyl groups. WO/2005/111224 discloses CoQ10 complexes with beta-cyclodextrin to increase CoQ10 solubility in water.

WO 00/38655A-1 describes formulations comprising porous calcium hydrogen phosphate particulates, sold commercially under the trademark, Fujicalin®, within which a liquid formulation of an active agent is absorbed, so that the liquid-absorbing particulates can be processed using conventional pharmaceutical equipment. These formulations are said to provide high concentrations of active drug dosage without loss of active pharmaceutical agent during the manufacturing process, and to permit delivery of active pharmaceutical agent, along with suitable solubilization-enhancers to an absorption site. Other forms of the porous particulates are also disclosed including microcrystalline cellulose, silicon dioxide, or magnesium aluminosilicate, or blends thereof.

U.S. patent Ser. No. 10/046,018 describes methods and formulations for increasing the water solubility and/or bioavailability of a phytocannabinoid compound. In one example, the water-soluble phytocannabinoid formulation comprises a phytocannabinoid and a non-ionic surfactant in a weight ratio of 1:10,000 to 1:5 phytocannabinoid to non-ionic surfactant. However, hydrogenation of cannabinoids is required to render them more water soluble, and the hydrogenation method results in decreased absorption and bioavailability of the cannabinoids. The formulation also undesirably includes an alcoholic solvent, such as methanol, ethanol, propanol or butanol, to dissolve the cannabinoids.

In view of the foregoing, it would be desirable to provide a stable, water soluble pharmaceutical formulation.

BRIEF DESCRIPTION OF THE INVENTION

A formulation that provides enhanced oral bioavailability of poorly water-soluble pharmaceutical agents is herein provided. The formulation comprises a pharmaceutical agent which is poorly water-soluble, a detergent, a lipase, a plasticizing agent and an emulsifying agent in an aqueous solvent.

Thus, in one aspect of the invention, a formulation is provided comprising a water-insoluble or poorly insoluble pharmaceutical agent, a detergent, a lipase, a plasticizing agent and an emulsifying agent in an aqueous solvent.

In another aspect of the invention a water-soluble formulation is provided comprising a cannabinoid, a detergent, a lipase, a plasticizing agent and an emulsifying agent.

These and other aspects of the invention are described by reference to the following Figure.

BRIEF DESCRIPTION OF THE FIGURE

FIG. 1 is a table illustrating the chemical structures of various cannabinoids.

DETAILED DESCRIPTION OF THE INVENTION

A formulation is provided comprising a water-insoluble or poorly insoluble pharmaceutical agent, a detergent, a lipase, a plasticizing agent and an emulsifying agent.

The present formulation comprises a water-insoluble or poorly insoluble pharmaceutical agent. The phrase "water-insoluble" as used herein is meant to encompass any pharmaceutical agent, i.e. an agent that possesses a therapeutic utility, that does not fully dissolve in a given aqueous solvent, including agents that are slightly soluble, sparingly soluble and completely insoluble, for example, an agent that requires greater than 30 mass parts of solvent to dissolve 1 mass part of solute (pharmaceutical agent), e.g. an agent that requires greater than 50, 100, 1000 or more, mass parts of solvent to dissolve 1 mass part of solute. Examples of water-insoluble pharmaceutical agents include, but are not limited to:

a. antimicrobial agents, such as triclosan, cetyl pyridium chloride, domiphen bromide, quaternary ammonium salts, zinc compounds, sanguinarine, fluorides, alexidine, octonidine, EDTA, and the like;

b. non-steroidal anti-inflammatory drugs, such as aspirin, acetaminophen, ibuprofen, ketoprofen, diflunisal, fenoprofen calcium, naproxen, tolmetin sodium, indomethacin, and the like;

c. anti-tussives, such as benzonatate, caramiphen edisylate, menthol, dextromethorphan hydrobromide, chlophedianol hydrochloride, and the like;

d. decongestants, such as pseudoephedrine hydrochloride, phenylepherine, phenylpropanolamine, pseudoephedrine sulfate, and the like;

e. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like;

f. expectorants, such as guaifenesin, ipecac, potassium iodide, terpin;

g. anti-diarrheals, such a loperamide, and the like;

h. $H_2$-antagonists, such as famotidine, ranitidine, and the like;

i. proton pump inhibitors, such as omeprazole, lansoprazole;

j. general nonselective CNS depressants, such as aliphatic alcohols, barbiturates and the like;

k. general nonselective CNS stimulants such as caffeine, nicotine, strychnine, picrotoxin, pentylenetetrazol and the like;

l. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like;

m. antiparkinsonism drugs such as levodopa, amantadine and the like;

n. opioid analgesics such as alfentanil, allylprodine, alphaprodine, anileridine, benzylmorphine, bezitramide, buprenoorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazine, fentanyl, heroin, hydrocodone, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, sufentanil, tramadol, tilidine, salts thereof, mixtures of any of the foregoing, mixed mu-agonists/antagonists, mu-antagonist combinations, free base forms, pharmaceutically acceptable salts, or in the form of a pharmaceutically acceptable complex;

o. analgesic-antipyretics such as salycilates, phenylbutazone, indomethacin, phenacetin and the like;

p. psychopharmacological drugs such as chlorpromazine, methotrimeprazine, haloperidol, clozapine, reserpine, imipramine, tranytcypromine, phenelzine, lithium and the like;

q. hypnotics, sedatives, antiepileptics, awakening agents;

r. vitamins and minerals, caffeine, nicotine;

s. amino acids and peptides;

t. compounds such as sildenafil citrate (Viagra etc);

u. proteins, hormones and peptides e.g., insulin, erythropoietin, etc.;

v. antidiabetic drugs, e.g., metformin, glyburide and insulin secretart agent, insulin stimulators, fat metabolizers, carbohydrates metabolizers, insulin, cholesterol lowering agents like statins, etc.;

w. a cannabinoid, terpene and analogues thereof;

x. pharmaceutically acceptable salts of any of the foregoing.

As used herein, the terms "cannabinoid" or "cannabinoid compound" refer to naturally occurring cannabinoids or terpenes from a Cannabis plant, typically from the Cannabis sativa or hemp plant, as well as analogues thereof, including synthetically prepared cannabinoids and analogues thereof. Exemplary cannabinoids include cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), cannabidivarin acid (CBDVA), cannabinovarin (CBNV), cannabinodiol (CBDL), cannabicyclol (CBL), cannabielsoin (CBE), cannabitriol (CBT), cannabivarin (CBV), cannabichromevarin (CBCV), cannabigerol monoethyl ether (CBGM), tetrahydrocannabinols (THC), tetrahydrocannabivarin (THCV), naphthoylindoles such as JWH-018, JWH-073, JWH-398, JWH-200, JWH-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenols such as CP 47,497-C8 and CP 47,497; HU-210 and pharmaceutically acceptable salts thereof.

The term "pharmaceutically acceptable salts" or "salts" is meant to include a salt of a pharmaceutical agent prepared with nontoxic or relatively non-toxic acids or bases, depending on the particular substituent moieties found on the compounds described herein. Examples of acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The present formulation will generally comprise the pharmaceutical agent in an amount in the range of about 1-50% by wt.

The present formulation comprises at least one biological detergent. Biological detergents contain one or more enzymes that break down lipids (including triglycerides, fats, oils), e.g. a lipase, one or more enzymes that break down proteins, e.g. a protease, and/or one or more enzymes that break down starches. The detergent may be an ionic, non-ionic or zwitterionic detergent. Detergents are amphipathic molecules, containing a polar hydrophilic head group attached to a long-chain hydrophobic carbon tail. The polar head group of ionic detergents contain either a positive (cationic) or negative (anionic) charge.

Anionic detergents typically have negatively-charged sulfate or sulfonate groups as the hydrophilic head; whereas cationic detergents contain a positively-charged ammonium group. Bile acids, such as cholic acid, deoxycholic acid, glycocholic acid, chenodeoxycholic acid, taurocholic acid, glycodeoxycholic acid, taurodeoxycholic acid, or a salts thereof, and aliphatic sulphate esters (e.g., sodium dodecyl sulphate or sodium lauryl sulfate) are examples of anionic detergents, and quaternary ammonium salts of acetates, chlorides, or bromides are examples of cationic detergents.

Non-ionic detergents have a neutral, polar head group. Non-ionic detergents are typically based on polyoxyethylene or a glycoside. Polyoxyethylene detergents have a tail composed of hydrophobic oxyethylene or ethylene glycoether chains. Examples of polyoxyethylene-based detergents include ethoxylates, PEGylates and metabolites thereof, including Tweens such as polysorbate 20 (polyoxyethylene (20) sorbitan monolaurate), polysorbate 40 (polyoxyethylene (20) sorbitan monopalmitate), polysorbate 60 (polyoxyethylene (60) sorbitan monostearate), polysorbate 80 (polyoxyethylene (80) sorbitan monooleate), alkylphenol ethoxylates such as nonoxynols and Triton™, and the Brij™ compounds, e.g. Brij 20 (polyoxyethylene (20) cetyl ether) or Brij 35 (polyoxyethylene (23) lauryl ether). Glycosidic-based detergents have a sugar, such as glucose or maltose, as their uncharged hydrophilic headgroup, and may have an alkyl polymer tail. Examples include octyl thioglucoside and maltosides. Fatty acid esters of sorbitol, such as sorbitan monolaurate, sorbitan monostearate and sorbitan tristearate, fatty acid esters of glycerol, such as glycerol monostearate and glycerol monolaurate and fatty acid esters of sucrose are also non-ionic detergents.

The polar head groups of zwitterionic detergents contain both negatively and positively charged atomic groups, therefore the overall charge is neutral, e.g. (dimethylmyristylammonio)-propanesulfonate and (tert-Butyl-1-pyridinio)-1-propanesulfonate. Other examples include 3-[(3-cholamidopropyl)dimethylammonio]-1-propanesulfonate (CHAPS) and 3-[(3-cholamidopropyl)-dimethylammonio]-2-hydroxy-1-propanesulfonate (CHAPSO).

As one of skill in the art will appreciate, the appropriate detergent for inclusion in the present formulation will depend on factors such as the pharmaceutical agent in the formulation, pH, ionic charges, the desired denaturing effect and the desired end result, including structure and charge of the final product.

Examples of enzymes that may be used in conjunction with the detergent to provide a biological detergent include, but are not limited to, lipases such as pancreatic lipase (PL), pancreatic lipase-related protein 1 or 2 (PLRP1/PLRP2), hepatic lipase, endothelial lipase, lipoprotein lipase, lysosomal lipase, gastric lipase and lingual lipase. Other examples include termamyl (amylase), lipolase (lipase), celluzyme (cellulase), mannanase and pectinase. The enzymes may be naturally occurring enzymes or recombinant enzymes. Individual enzymes or combinations of enzymes may be used.

The amount of detergent in the present formulation is in the range of about 0.01 to 10% by wt of the composition. The amount of enzyme in the formulation is in the range of about 0.01 to 10% by wt of the composition.

The present formulation includes one or more plasticizing agents to attain desired flexibility and mold-releasing properties. Suitable plasticizing agents include, for example, triacetin, monoacetin, diacetin and glycerin. Plasticizing agent may be added to the formulation in an amount ranging from about 0.01 to about 20 wt %, preferably an amount of about 0.1 to about 2 wt % of the formulation.

The present formulation also includes an emulsifying agent such as triethanolamine stearate, quaternary ammonium compounds, acacia, gelatin, lecithin, bentonite, veegum, and the like, in amounts ranging from about 0.01 to about 5 wt %, and preferably about 0.01 to about 0.7 wt % of the formulation.

The present formulation may include a stabilizing agent such as xanthan gum, locust bean gum, guar gum and carrageenan, in amounts ranging from about 0.01 to about 10 wt %, preferably about 0.1 to about 2 wt % of the formulation.

The present formulation may also include one or more saliva stimulating agents such as a food acid, e.g. citric, lactic, malic, succinic, ascorbic, adipic, fumaric or tartaric acid, or mixtures thereof. Preferred food acids are citric, malic and ascorbic acids. The amount of saliva stimulating agent suitable for inclusion in the present formulation may range from about 0.01 to about 12 wt %, preferably about 1 wt % to about 10 wt %.

The present formulation may additionally include a thickening agent such as methylcellulose, carboxyl methylcellulose, and the like, in amounts ranging from about 0.01 to about 20 wt %, and preferably about 0.01 to about 5 wt %.

The present formulation may further include one or more pharmaceutically acceptable adjuvants or carriers. The expression "pharmaceutically acceptable" means acceptable for use in the pharmaceutical arts, i.e. not being unacceptably toxic, or otherwise unsuitable for administration to a mammal. Examples of pharmaceutically acceptable adjuvants include, but are not limited to, diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the invention, the compounds are formulated for oral administration via tablet, capsule, lozenge, solution or suspension in an aqueous or non-aqueous liquid, an oil-in-water or water-in-oil liquid emulsion, an elixir or syrup are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions, wetting agents, lubricants, stabilizers, anti-oxidants and preservatives.

To render the formulation more desirable for oral administration, natural and/or artificial sweeteners, flavouring agents and colouring agents may be included in the formulation.

Suitable sweeteners include, water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like; dipeptide based sweeteners, such as L-aspartic acid derived sweeteners, such as L-aspartyl-L-phenylalanine methyl ester (aspartame) and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexyen)-alanine, and the like; derivatives of water-soluble sweeteners such as a chlorinated derivative of sucrose, i.e. sucralose; and protein based sweeteners such as *Thaumatoccous danielli* (Thaumatin I and II). In general, an effective amount of an auxiliary sweetener is utilized to provide the desired level of sweetness. The amount of sweetener will vary with the selected sweetener. Generally, an amount of sweetener in the range of 0.01% to about 10% by weight of the formulation is appropriate.

Flavorings that may be used in the formulation include both natural and artificial flavors. These flavorings may be chosen from synthetic flavor oils and flavoring aromatics and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as lemon, orange, grape, lime, grapefruit, apple, pear, peach, strawberry, raspberry, cherry, plum, pineapple, apricot and so forth. These flavorings may be used individually or in admixture. Other flavours include vanilla, chocolate and coffee. Aldehydes and esters may be used as flavourants as well, e.g. cinnamyl acetate, cinnamaldehyde, citral, diethylacetal, dihydrocarvyl acetate, eugenyl formate, p-methylanisole, acetaldehyde (apple); benzaldehyde (cherry, almond); cinnamic aldehyde (cinnamon); citral, (lemon, lime); decanal (orange, lemon); ethyl vanillin (vanilla, cream); heliotropine, i.e., piperonal (vanilla, cream); vanillin (vanilla, cream); butyraldehyde (butter, cheese); valeraldehyde (butter, cheese); citronellal (modifies, many types); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like. The amount of flavoring employed may be in the range of about 0.1 to about 30 wt %.

The formulation may also contain coloring agents or colorants. The coloring agents may include natural food colors and dyes suitable for consumption such as FD&C dyes and lakes, such as FD&C Blue No. 2, which is the disodium salt of 5,5-indigotindisulfonic acid and FD&C Green No. 3 which is the monosodium salt of 4-[4-N-ethyl-p-sulfobenzylamino) diphenyl-methylene]-[1-N-ethyl-N-p-sulfonium benzyl)-2,5-cyclo-hexadienimine]. FD&C and D&C dyes and their corresponding chemical structures are described in the *Kirk-Othmer Encyclopedia of Chemical Technology*, Volume 5, pages 857-884. Pigments such as titanium dioxide may be used. Colorants may be incorporated in amounts of up to about 5 wt %, and preferably less than about 1 wt %.

Cooling agents may be added to the formulation to increase the boiling point thereof. Examples of cooling agents that may be added to the formulation are monomenthyl succinate, WS3, WS23 and Ultracool II in an amount ranging from about 0.001 to about 2.0 wt %, preferably about 0.2 to about 0.4 wt % of the formulation.

The balance of the formulation is an aqueous solvent such as water or other water-containing solvent, e.g. saline, etc.

The present formulation may be in the form of a beverage, juice, soft drink, bottled water or a liquid concentrate.

The present formulation may be prepared as follows. The selected pharmaceutical agent is added to a volume of the selected detergent or mixture of detergents and heated to a temperature in the range of about 35-65° C. The heated combination is mixed to form a clear emulsion in which the pharmaceutical agent is dissolved, e.g. generally with high speed mixing. Hot water may additionally be added to the combination to achieve dissolution, e.g. a crystal clear solution. Other non-aqueous components may then be added with heat and stirring. An aqueous solution comprising water-soluble components (e.g. sweetener, flavor, colour) is then added to the emulsion and mixed to form a clear solution. Enzyme, plasticizer, saliva stimulating agent, stabilizing agent and any additional emulsifying agent are added once the solution or suspension is made. The mixture is further stirred to form a clear or almost clear solution, and then allowed to cool for storage.

The present invention advantageously provides an oral formulation in which water insoluble pharmaceutical agents are solubilized without using alcohols, i.e. an alcohol-free formulation. In addition, the formulation is prepared using hydrogenation methods to form a clear aqueous solution that exhibits improved bioavailability. As used herein, the term "clear" is intended to relate to a solution or aqueous solution that is free, or essentially free, of visible particles of undissolved compound. A clear solution or clear aqueous solution includes, thus, both solutions as well as very fine dispersions that remain clear upon sitting undisturbed for one hour or more. Essentially in a clear solution no visible (to the naked eye) particles or micelles are present.

Embodiments of the invention are described in the following specific examples which are not to be construed as limiting.

Example 1

A formulation comprising the water insoluble pharmaceutical agent, cannabidiol (CBD), was prepared with the following ingredients:
0.01-50% CBD oil
5% vitamin E (d,l-α-tocopheryl acetate) (emulsifier)
1-15% omega-3 fatty acid ethyl ester (Incromega™ 3322) (emulsifier)
15% mono-, di-glycerides of caprylic acid (detergent)
20% polyoxyl 35 (Cremophor™ EL) (emulsifier)
3% Na lauryl sulfate (SLS) (ionic detergent)
0.1-25% glycerin (plasticizing agent)
2% Brij 80 detergent (Tween)
5% triethanolamine stearate (emulsifier)
3% pancreatic lipase related protein 2 and 1 (lingual lipase)
0.1% sodium citrate (saliva stimulating agent)
27% distilled water The method of making the present formulation was as follows. A water soluble formulation comprising cannabidiol and THC was prepared by admixing the cannabidiol oil with the detergents, Na lauryl sulfate+Brij 80 (polyoxyl ether 80). The cannabidiol oil contained 80 wt % cannabidiol (CBD) and 20% oil. The mixture was heated with stirring to a temperature of about 60° C. and mixed at 1000-1500 rpm until a clear viscous emulsion phase with dissolved CBD oil was formed (cannabidiol emulsion). Water was boiled at 212° F. The heated water was then slowly added to the cannabidiol emulsion until a crystal clear solution was formed. In a separate container, Vitamin E ail, Omega-3 oil fatty acid ethyl ester, mono/di-glyceride of caprylic acid detergent, Cremophor, glycerin and Tween were combined and mixed to form an emulsion. This emulsion was then added slowly to the oil-water mixture at 60° C. slowly while stirring continuously at 1000 rpm. An aqueous solution comprising water-soluble components, if any (e.g. sweetener, flavor, colour), are then added to the emulsion and mixed to form a clear solution. Enzyme, saliva stimulating agent and emulsifying agent (triethanolamine stearate) were then added to the solution. The mixture thus prepared was stirred additionally for 30-45 minutes to form an essentially clear solution. The solution was then cooled down slowly to room temperature and stored in a brown glass bottle.

Example 2

A water soluble formulation comprising cannabidiol (CBD) was prepared by admixing cannabidiol oil with the ionic detergents, Na lauryl sulfate+Brij 80 (polyoxyl ether 80). The cannabidiol oil contained 80 wt % cannabidiol (CBD). The ionic detergents were heated and stirred to a temperature of about 120° F. Then the cannabidiol oil was added slowly and mixed at 1000-1500 rpm until a clear viscous emulsion phase with dissolved CBD oil was formed (cannabidiol emulsion). Water was boiled at 212° F. The heated water was then slowly added to the cannabidiol emulsion until a crystal clear solution was formed. The remaining ingredients were then added.

The weight percentage of each component in the water soluble composition is presented in Table 1.

| Formulation | wt % |
|---|---|
| CBD | 5.000 |
| Avicel | 0.250 |
| Thymol NF | 0.400 |
| Menthol NF | 0.550 |
| Methyl Salicylate | 0.500 |
| Mint flavor | 8.500 |
| Citric Acid | 0.750 |
|  | (saliva stimulating agent) |
| Copper gluconate | 1.250 |
| Purified water, USP | 68.500 |
| Sodium lauryl sulfate | 1.500 |
|  | (surfactant, detergent) |
| Aspartame | 6.500 |
|  | (sweetener) |
| Cooling agent | 0.075 |
| Sorbitol (crystalline) | 1.000 |
|  | (sweetener) |
| Glycerin | 5.000 |
|  | (plasticizer) |
| Polysorbate 80 NF | 0.550 |
|  | (emulsifier) |
| Atmos 300 | 0.550 |
|  | (emulsifier) |
| FD&C Green #3 | 0.009 |
| Macrogolglycerol | 13.116 |
| D&C Yellow #10 | 0.002 |
| Lipase | 0.003 |

Example 3

A water soluble formulation comprising cannabidiol was prepared as follows. Polyoxyl 40 castor oil (Brij 80) was heated and stirred to a temperature of about 100° F. Then grapefruit seed oil (a natural preservative) and a cannabidiol oil containing 80 wt % cannabidiol (CBD) were added slowly and mixed until a clear viscous solution was formed. The clear emulsion was then slowly added to warm water (120° F.-180° F.) until a crystal clear solution was formed and then remaining ingredients were added.

The weight percentage of each component in the formulation was as follows:

| Ingredient | Wt % |
|---|---|
| Grapefruit seed Extract Oil | 0.5 |
| Cannabidiol Oil (80% CBD) | 2.0 |
| Water | 62.45 |
| Sodium Lauryl Sulfate + Brij 80 | 10.0 (surfactant/detergent - 5 wt % each) |
| Glycerin | 10.0 (plasticizer) |
| Cooling agent | 0.0750 |
| Sorbitol (crystalline) | 5.0000 |
| Aspartum | 10.000 |
| Green color | 0.05 |
| Citric Acid | 0.2 (saliva stimulating agent) |
| Polysorbate 80 NF | 0.550 (emulsifier) |
| Atmos 300 | 0.550 (emulsifier) |
| Lipase | 0.0030 |

Example 4

A pharmacokinetic, bioavailability (blood absorption) study was conducted with the water soluble cannabidiol formulation from Example 2 above to compare the bioavailability of cannabinoids in the formulation as compared to cannabinoid oil.

Male Sprague-Dawley rats (mean wt 0.298 kg) were administered 50 mg doses by oral gavage. Blood plasma samples were collected at various intervals from 0-24 hours, post dose, and the plasma concentration of cannabidiol was determined by liquid chromatography/tandem mass spectrometry (LC-MS/MS). The animal data collected is shown below and displays the mean blood plasma level over a 24 hour period.

Plasma Conc'n of CBD (Ng/Ml)

| Time | Formulation | *Cannabis* Oil |
|---|---|---|
| 0 hour (pre-dose) |  |  |
| 0.25 hour | 103 | 14.6 |
| 0.5 hour | 342 | 19.2 |
| 1.0 hour | 681 | 91.7 |
| 2.0 hours | 3470 | 265 |
| 4.0 hours | 2370 | 192 |
| 8.0 hours | 1570 | 127 |
| 24 hours | 551 | 30.6 |

Consumption of the present formulation resulted in a much greater plasma concentration of CBD than consumption of CBD oil itself. The $C_{max}$ of the present formulation 2310 ng/ml as compared to 192 for CBD oil itself. Thus, bioavailability of CBD was significantly improved using the present formulation, e.g. 76.9% uptake of CBD when administered the present formulation vs. 6.3% CBD uptake for CBD oil.

The total absorption level AUC∞ (hr·kg·ng/mL/mg) was determined to be 89 for CBD oil as compared to 296 for the present water-soluble CBD formulation.

The invention claimed is:

1. A formulation comprising: a water-insoluble pharmaceutical agent in an amount of 1%-50% by weight of the formulation, a detergent in an amount of 0.01% to 10% by weight, lipase in an amount of 0.01 to 10 wt %, a plasticizing agent in an amount of 0.01% to about 20% by weight, an emulsifying agent in an amount of 0.01% to about 20% by weight and an aqueous solvent as the balance of the formulation, wherein the pharmaceutical agent is solubilized or dissolved in the formulation.

2. The formulation of claim 1, wherein the water-insoluble pharmaceutical agent is a cannabinoid or an analogue or salt thereof.

3. The formulation of claim 2, wherein the cannabinoid is selected from the group consisting of cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), cannabidivarin acid (CBDVA), cannabinovarin (CBNV), cannabinodiol (CBDL), cannabicyclol (CBL), cannabielsoin (CBE), cannabitriol (CBT), cannabivarin (CBV), cannabichromevarin (CBCV), cannabigerol monoethyl ether (CBGM), tetrahydrocannabinol (THC), tetrahydrocannabivarin (THCV), naphthoylindoles; phenylacetylindoles; benzoylindoles; cyclohexylphenoles; and pharmaceutically acceptable salts thereof.

4. The formulation of claim 1, wherein the detergent comprises an ionic, non-ionic or zwitterionic detergent.

5. The formulation of claim 1, wherein the lipase is selected from the group consisting of pancreatic lipase (PL), pancreatic lipase-related protein 1 (PLRP1), pancreatic lipase-related protein 2 (/PLRP2), hepatic lipase, endothelial lipase, lipoprotein lipase, lysosomal lipase, gastric lipase, lingual lipase and lipolase.

6. The formulation of claim 4, wherein the detergent is selected from the group consisting of a bile acid or a salt thereof, and an aliphatic sulphate ester.

7. The formulation of claim 1, comprising 0.01 to about 12 wt % of a saliva stimulating agent selected from citric acid, lactic acid, malic acid, succinic acid, ascorbic acid, adipic acid, fumaric acid, tartaric acid, and mixtures thereof.

8. The formulation of claim 1, wherein the plasticizing agent is selected from triacetin, monoacetin, diacetin and mixtures thereof.

9. The formulation of claim 1, comprising 0.01 to about 10 wt % of a stabilizing agent selected from xanthan gum, locust bean gum, guar gum, carrageenan and mixtures thereof.

10. The formulation of claim 1, wherein the emulsifying agent is selected from triethanolamine stearate, a quaternary ammonium compound, acacia, gelatin, lecithin, bentonite, veegum, and mixtures thereof.

11. The formulation of claim 1, which is an oral formulation.

12. The formulation of claim 11, which is a beverage.

13. The formulation of claim 1, wherein said formulation is an injectable formulation.

14. The formulation of claim 1, additionally comprising a saliva stimulating agent.

15. A method of making a formulation as defined in claim 1, comprising:
   i) combining the pharmaceutical agent and the detergent with heat to form a clear emulsion in which the pharmaceutical agent is solubilized or dissolved;
   ii) adding heated aqueous solvent to the clear emulsion to form a clear solution;
   iii) adding to the clear solution an emulsion comprising the lipase, plasticizer and emulsifying agent; and
   iv) stirring the emulsion of step iii) with the clear solution and allowing the solution to cool.

16. The method of claim 15, wherein the pharmaceutical agent is a cannabinoid.

17. The method of claim 16, wherein an aqueous solution of water-soluble ingredients is added to the clear solution in step ii).

18. The method of claim 17, wherein the water-soluble ingredient is selected from the group consisting of sweeteners, flavouring agents, colouring agents and mixtures thereof.

19. The method of claim 16, wherein the detergent comprises sodium lauryl sulfate and a polyoxyethylene detergent and the plasticizing agent is glycerin.

20. The formulation of claim 1, wherein the detergent comprises sodium lauryl sulfate and a polyoxyethylene detergent and the plasticizing agent is glycerin.

* * * * *